United States Patent [19]

Weinberg

[11] Patent Number: 5,714,584

[45] Date of Patent: Feb. 3, 1998

[54] CROSS-LINKED OXYGEN BINDING PROTEINS

[76] Inventor: Steven L. Weinberg, P.O. Box 580644, Houston, Tex. 77258-0644

[21] Appl. No.: 488,121

[22] Filed: Jun. 7, 1995

[51] Int. Cl.$^6$ .............................. A61K 35/14; C07G 3/00
[52] U.S. Cl. .................... 530/385; 530/380; 204/157.68; 204/157.15; 204/157.6; 514/21
[58] Field of Search ....................... 530/385, 380; 204/157.68, 157.15, 157.6; 514/21

[56] References Cited

U.S. PATENT DOCUMENTS 5,147,514   9/1992   Mechanic ........................... 204/157.68

OTHER PUBLICATIONS

Ginotti et al, *Photochemistry and Photobiology*, vol. 29, pp. 1119-1125, 1979.
Girotti, Albert W., Lyman, Suzanne and Deziel, Mark R., "Methylene Blue–Sensitized Photooxidation of Hemoglobin: Evidence for Cross-Link Formation," Photochemistry and Photobiology, vol. 29, pp. 1119–1125 (Great Britain, 1979).

*Primary Examiner*—Cecilia J. Tsang
*Assistant Examiner*—Abdel A. Mohamed
*Attorney, Agent, or Firm*—Mark R. Wisner

[57] ABSTRACT

The present invention relates to artificial blood and blood substitutes and supplements made by a process for cross-linking a proteinaceous material including an oxygen transport/binding protein such as hemoglobin, methhemoglobin, myoglobin and hemocyanin. The process comprises: i) soaking the proteinaceous material including the oxygen transport/binding protein to be cross-linked in an aqueous solution of high osmolality; ii) incubating the material in an aqueous buffer including an amount of a photooxidative catalyst sufficient to catalyze photooxidation of the material; and iii) irradiating the material and the catalyst of step (i) with light that includes a range of wavelengths selectively absorbed by the catalyst. Irradiation is effected under conditions such that cross-linking of the material occurs.

14 Claims, No Drawings

CROSS-LINKED OXYGEN BINDING PROTEINS

TECHNICAL FIELD

This invention relates, in general, to an implantable tissue resulting from a process for cross-linking and stabilizing proteinaceous material, and in particular, to artificial blood resulting from a process for photooxidizing hemoglobin, myoglobin, and other oxygen binding proteins in the presence of a photo-catalyst to cross-link and stabilize those proteins.

BACKGROUND OF THE INVENTION

Reagents and processes currently used for protein cross-linking generally depend upon the incorporation of the cross-linking reagent into the protein matrix to cross-link the e-amino groups of lysine, hydroxylysine, and/or other groups in the protein. Common cross-linking reagents in such processes include formaldehyde and glutaraldehyde; other processes include the introduction of a phthaloyl or adipoyl moiety into the protein via phthaloyl dichloride or adipoyl dichloride, respectively, and/or the introduction of a mercaptan for oxidation to a disulfide bond.

The cross-linking processes, reactions and reagents of the prior art vary, but most involve incorporating the reagent into or around the protein. For example, recent data by Cheung and Nimni (Connec. Tissue Res. 10:201 (1982) and Connec. Tissue Res. 13:109 (1984) on the cross-linking reagent glutaraldehyde indicate that when this reagent is used to treat collagen fibrils, for example, a polymeric-like coating forms around the fibrils, resulting in stiffer collagen matrix.

In contrast, the cross-linked product made by the method disclosed herein does not depend upon the incorporation of a cross-linking reagent into the protein to be cross-linked or the coating of the protein with a cross-linking reagent. The present process involves the use of photooxidative dye which acts as a cross-linking oxidation catalyst or promotor and which can be removed from the cross-linked product.

The use of photooxidative catalysts in various photooxidation processes has been previously reported (see e.g., Ray, Method in Enzymol. 11:490 (1967); Westhead, Biochem 4:10 (1965); Ray and Koshland, Jr., J. Biological Chem. 18:409 (1967); Foote, Science 162:3857 (1968); and Girotti, et al., Photochemistry and Photobiology 29:1119 (1979)). However, they either do not appear to have been used for cross-linking proteinaceous materials or do not suggest uses for such materials. For instance, Ray and Koshland, Jr., supra, used methylene blue and light to photooxidize the enzyme phosphoglucomutase in an attempt to identify the amino acid residues of that protein which are essential to the activity of the enzyme by selective destruction of amino acids. Likewise, Westhead, supra, inactivated yeast enolase by photooxidation of histidine residues with the dye rose bengal.

Excitation of a dye by light has also been used to covalently couple the dye to a protein (Brandt, et al., Biochemistry 13:4758 (1974)), and that technique has led to a method of dye-sensitized photolabeling of proteins (Brandt, et al., Anal. Biochem. 93:601 (1980)). Although the technique is useful for such purposes as the study of the molecular arrangement of proteinaceous membrane components (Id.) and protein conformation (Hemmendorff, et al., Biochem. Biophys. Acta 667:15 (1981)), the technique does not appear to introduce iner- and/or intra-molecular cross-links into the protein matrix.

The above-cited Girotti, et al. reference discloses the photooxidative cross-linking of hemoglobin using a dye such as methylene blue as a photosensitizing agent. That reference, however, does not teach the use of the cross-linked proteinaceous product as an implantable tissue, suggesting only that the results reported in that reference may have implications relating to the general problem of photodynamic damage in red blood cells and stating that it was safe to assume that cross-linking affects the ability of hemoglobin to combine with oxygen.

A dye-catalyzed process said to be useful for preparing thermostable, irreversibly cross-linked collagenous polymers is described in U.S. Pat. No. 3,152,976. This patent alleges that the product resulting from that process is characterized by certain physical-chemical properties similar to those obtained by prior art tanning processes. However, the data presented in that patent do not support a conslusion that the product of that process possesses the properties which would make that product a useful biomaterial. Instead, that reference states that the product is more susceptible to enzymatic degradation than "uncross-linked" collagen. Such results are, of course, totally contrary to the use of such a product as, for instance, a heart valve (imagine a heart valve digested by even the mildly proteolytic enzyme papain in hours, or even seconds, as described in Example VII of that reference).

The results reported in the '976 patent can perhaps be explained by a close examination of the process described therein. For instance, the reference describes the preparation of a "starting material" on which the process set out in that patent is conducted by dispersing collagenous material in aqueous acid solution. Acid has the well-known effect of denaturing the protein comprising the collagen fibril. It is, of course, the three-dimensional structure of the proteins comprising the collagen fibril which imparts to the fibril the unique properties of collagen; change that structure and the protein cannot interact in the manner needed to give rise to those properties. A further explanation for the results described in that patent is suggested by P. H. von Hipple, "Structural and Stabilization of the Collagen Molecule in Solution" (in Treatise on Collagen, Vol. 1: Chemistry of Collagen, G. N. Ramachandran (Ed.), London: Academic Press Inc. (London) Ltd. (1967), pp. 253–338 at 262), reporting that collagen molecules extracted by acid and neutral salt procedures differ in the extent to which they are covalently cross-linked, size, shape, interaction properties and rate of fiber formation. Although based on preliminary data such that the author was careful to point out that results had been reported by other investigators which did not show any differences, subsequent experimentation supports the existence of such differences.

In light of this prior art, it is surprising that photooxidation of an oxygen binding/transport protein such as hemoglobin in the presence of a photo-catalyst and sufficient oxygen, under controlled conditions of pH and temperature, cross-links and stabilizes the protein to provide a product which can be used as a component of artificial blood without adverse effect on the functions and physical parameters of the protein in blood. It is especially surprising that such a cross-linked product will function for this purpose in light of the statement in the Girotti, et al., reference that it was safe to assume that cross-linking hemoglobin by the method described in that reference affects the ability of hemoglobin to combine with oxygen.

OBJECTS OF THE INVENTION

An object of this invention is to provide a stable cross-linked product which is usable as a component of artificial blood.

Another object of the present invention is to provide a composition of matter which is usable in place of whole blood which contains an oxygen binding/transport protein which has been cross-linked in accordance with the method of the present invention.

Other objects of the invention, as well as the several advantages of the invention, will be apparent to those skilled in the art upon reading the specification, the examples and the appended claims.

SUMMARY OF THE INVENTION

In accordance with the present invention, there is provided a component for use in blood or in an aqueous suspension which is used as a substitute for blood whereby an oxygen binding/transport protein is efficiently and effectively cross-linked and stabilized by subjecting such material to photooxidation in the presence of a photo-catalyst. In one embodiment, the present invention relates to the product of a process for cross-linking an oxygen transport/binding protein which comprises: i) soaking the protein to be cross-linked in an aqueous buffer of high osmolality; (ii) incubating the protein in an aqueous solution including sufficient photooxidative catalyst to catalyze the formation of inter- and intramolecular cross-links by oxidation of the material; and (iii) irradiating the protein and the catalyst of step (i) with light that includes a range of wavelengths selectively absorbed by the catalyst. Irradiation is effected under temperature and pH conditions, and an oxygen concentration, such that cross-linking of the protein occurs. This cross-linked product is used as a supplement in whole blood to, for instance, increase the oxygen binding and/or transport capabilities of the blood (e.g., for anemic patients), is encapsulated in lipid membranes in accordance with known encapsulation techniques and the capsules suspended in an aqueous liquid which is provided with various salts and sugars so as to physiologically compatible with the blood of the patient, or inserted into the membranes of reb blood cells. When so used, the products of the present invention are superior to naturally-occurring hemoglobin for they retain the mechanical properties of the pre-treated material, are non-immunogenic, and are resistant to in vivo degradation. Therefore the cross-linked product of the present invention is superior to the biomaterials known in the art for use in these applications.

DETAILED DESCRIPTION OF THE INVENTION

The process of the present invention provides an efficient and effective method for cross-linking and stabilizing various proteinaceous materials including, but not limited to hemoglobin, methemoglobin, myoglobin, hemocyanin, and the oxygenated forms of these oxygen binding/transport proteins. The term proteinaceous material as used herein includes both these several binding/transport proteins and protein-containing materials such as tissues, e.g., the muscle or blood in which the protein(s) are contained. As a general rule, the particular proteineious material utilized as the starting material is determined by the intended use of the product. For instance, if it is desired to make a hemoglobin-containing suspension which is useful as a supplement to the blood of a patient during, for instance, a surgical procedure, the material to be cross-linked can be provided as a tissue sample, e.g., as whole blood. Such materials are harvested from a donor animal and immediately immersed in cold buffered saline for storage, with frequent rinses and/or changes with fresh saline, until processed in accordance with the process described herein.

The proteinaceous material to be photooxidized is then isolated using known separation techniques, and immersed, dispersed, or suspended (depending upon its previous processing) in an aqueous media for processing in accordance with the present invention. Suitable media for immersion of the proteinaceous material (for purposes of convenience, the word "immersion" shall be considered to include suspension and/or solubilization of the proteinaceous material) include aqueous and organic buffer solutions having a neutral to alkaline pH, preferably a pH of about 6.5 and above because of the denaturation caused by acid pH. Particularly preferred are buffered aqueous solutions having a pH of from about 6.8 to about 8.6. Examples of media that can be used herein include:

1. water or low ionic strength buffers;
2. phosphate buffered saline;
3. high ionic strength buffers ($\mu$=1.75–3.0) and
4. organic buffers containing potassium or sodium phosphate, or potassium or sodium chloride, such as Good's buffer (e.g., HEPES, TES or BES—Research Organics, Inc.).

The media may also contain the photocatalyst, which is preferably soluble therein.

In a particularly preferred embodiment, two media solutions are utilized for what is referred to herein as "preconditioning" the proteinaceous material before irradiation. The material is "preconditioned" in the sense that materials soaked in the first media solution and irradiated in the second are apparently better cross-linked, e.g., they show decreased susceptibility to proteolytic degradation. The efficacy of this preconditioning is affected by the osmolality of the first media solution, it being preferred that solutions of high osmolality be used as the first media solution. Particularly preferred are sodium, potassium, or organic buffer solutions such as sodium chloride, sodium phosphate, potassium chloride, and Good's buffers having a pH of from about 6.8 to about 8.6, the osmolality of which have been increased by addition of a solute such as 4M sucrose or other soluble, high molecular weight carbohydrate to between about 393 mosm and about 800 mosm.

The solute added to increase the osmolality of the first media appears to have an adverse effect on the degree of cross-linking of the product when present during irradiation. Consequently, after soaking in the first media, proteinaceous materials are preferably removed therefrom and immersed in a second mdeia for irradiation. The second media is preferably an aqueous buffered solution having a pH of from about 6.8 to about 8.6 in which the photo-catalyst is dissolved. Preferred second media are sodium and potassium phosphate buffers having a pH of from about 7.4 to about 8.0 and an osmolality of from about 150 to about 400 mosm, 300±10 mosm being particularly preferred.

The material to be cross-linked is advantageously immersed sequentially in the first media and then in the catalyst-incorporated second media prior to photooxidation for a total period of time sufficient to allow tissue, dye, and medium to reach equilibrium. When the ratio of the concentration of the medium to that of the material to be cross-linked is in the range of from about 10:1 to 30:1, equilibrium can generally be readily achieved. The ratio of the concentrations is generally not critical, and may be adjusted up or down as desired. Once an equilibrium is reached, the sample is photooxidized in the catalyst-incorporated medium. The time required to reach equilibrium varies depending upon such factors as, for instance, the temperature of the media solutions, the osmolality of the first media, and the concentration of the tissue or other sample of proteinaceous material. A period of time as short as a few minutes or as long as several days may be sufficient, but periods of from minutes to hours duration are generally sufficient to allow sufficient time for most materials and media to equilibrate.

Generally speaking, the suitability of a catalyst for use in the present process is dependent upon the ability of the catalyst to be sensitized into an exited state (T.) where it serves as a photosensitizer. The substrate then reduces the (T.) state of the sensitizer by electron transfer. Studies have provided evidence that the substrate reacts initially with triplet state catalyst, producing secondary reactive radicals by electron or H atom transfer reactions. See, Spikes and Straight, Ann. Rev. Phys. Chem. 18:409 (1967).

The catalysts contemplated for use herein are photooxidative catalysts (photo-catalysts) that when activated will cause transfer of electrons or hydrogen atoms and thereby oxidize a substrate in the presence of oxygen. Although varied results are possible depending upon the particular catalyst utilized, appropriate catalysts include, but are not limited to, those listed in Oster, et al., J. Am. Chem. Soc. 81:5095, 5096 (1959). Particularly preferred catalysts include methylene blue, methylene green, rose bengal, riboflavin, proflavin, fluorescein, eosin, and pyridoxal-5-phosphate.

The concentration of catalyst in the media will vary based on several process parameters, but should be sufficient to insure adequate penetration into the material to be cross-linked and to catalyze the photooxidation of the oxygen transport/binding protein. A typical catalyst concentration ranges from about 0.0001%–0.25% (wt/vol); the preferred concentration ranges from about 0.01 to about 0.1%. To achieve maximum cross-linking and stabilization of the proteinaceous product, the following steps should be taken: (1) the photooxidative catalyst should be completely solubilized in the reaction medium prior to use to ensure that the desired dye concentration is achieved; (2) the concentration of the catalyst in the tissue or suspension should be in equilibrium with that in the surrounding medium; and (3) the catalyst solution should be filtered to remove any sizable particulate matter, including chemical particulates, therefrom.

Because the present invention involves primarily an oxidation reaction, to assure completion of the reaction, an adequate supply of oxygen must be provided during photooxidation. While an oxygen concentration of about 20% by volume (referring to the concentration of oxygen in the atmosphere over the media) is preferred to assure sufficient dissolved oxygen in the media to prevent oxygen content from becoming rate limiting, concentrations>0% and ranging up to 25% can also be used. Depending upon the temperature at which the proteinaceous material is held during exposure to light, the oxygen requirement can be met, for instance, by agitating the solution or otherwise mixing the solution, suspension, or sample during the reaction process. Oxygen concentration in the atmosphere over the media during irradiation is preferably maintained in the range of from about 5% to about 20%. Such concentrations (again depending upon temperature) can also be achieved, for instance, by bubbling air into the media during irradiation of the proteinaceous material or, if concentrations higher than about 20% are desired, by bubbling oxygen mixtures or air having an increased oxygen content into the media.

As with other catalytic or kinetic-type reactions, the temperature at which the reaction is run directly affects the reaction rate and the oxygen available in the media. Tests conducted with various media ranging in pH from about 6.8 up to about 7.4 and having an osmolality of 300±10 mosm indicate that as the temperature of the media increases from about 4° C. to about 50° C., oxygen concentration drops in roughly linear fashion from about 11–12 ppm to about 5 ppm. The dye-catalyzed photooxidation process of the present invention is exothermic, and it is, therefore, preferred that a relatively constant temperature be maintained during irradiation of the proteinaceous material to prevent denaturation of the proteinaceous material and the driving of the oxygen out of the media by the increase in temperature. Usually, a recirculating bath is sufficient to maintain and control the temperature within the jacketed reaction vessel or chamber, but placement of the reaction chamber within a controlled environment such as a refrigerator or freezer will work as well. As disclosed herein, photooxidation conducted at temperatures ranging from about −2° C. to +40° C. has been shown to be effective.; the preferred temperatures are from about 0° to about 25° C. To prevent or alleviate denaturation of the oxygen binding/transport protein comprising the proteinaceous material, temperatures below the denaturation temperature of that protein are preferred. Likewise, temperatures above the freezing point of the reaction medium are also preferred.

It is the combination and/or interaction of the variables of temperature, pH, and oxygen concentration described herein which is believed not to have been previously identified as critical in photooxidative cross-linking. Hence, the process of the present invention is conducted at temperatures low enough to avoid heat denaturation and pH high enough to avoid acid denaturation of the proteinaceous material during cross-linking. Likewise, temperature is held at a level sufficient to maintain the oxygen concentration in the media in which the proteinaceous material is immersed during irradiation.

Once the solution, suspension, or sample is prepared, it is photo-irradiated, preferably in a controlled system wherein temperature, distance to light source, irradiation energy and wavelenghth, oxygen concentration and period of irradiation can be monitored and/or maintained. The solution, suspension, or sample of proteinaceous material is photo-irradiated under conditions sufficient to cause cross-linking. Photooxidation is generally achieved using incandescent, white light or fluorescent light, i.e., visible light, or that portion of light in the visible range that is absorbed by the catalyst. Inexpensive light sources such as household bulbs, fluorescent lights and flood lamps are suitable for use herein.

The intensity of the light employed, and the length of time required to cross-link a given proteinaceous material will vary depending upon several factors. These include: (1) the type and amount of proteinaceous material; (2) the concentration of the tissue sample in the media; (3) the distance between the proteinaceous material and the irradiation source; (4) the catalyst employed; (5) the concentration of catalyst; and (6) the type and intensity of the light source. For instance, exposure time may vary from as little as a few seconds up to as much as about 160 hours. With regard to the intensity of the light, one or more lights may be used of intensity preferably ranging up to about 150 watts, preferably held at a distance from about 2.5 cm to 12 cm from the sample surface. Greater exposure time is required when fluorescent or lower power lights are utilized. These ranges are quite variable; however, they may be easily determined for a given material without resort to undue experimentation using the disclosure and examples provided herein as a guide. In a presently preferred embodiment, the intensity of the light and the exposure time is conveniently expressed in lumen hours, and when common fluorescent lights are used as the light source, a range of from about 100 to about 20,000 lumen hours is utilized for cross-linking most samples of proteinaceous material.

Evidence of the cross-linking of the oxygen binding/transport protein comprising the proteinaceous material by photooxidation in the presence of a catalyst in accordance with the process of the present invention is provided by several tests. For instance, polyacrylamide gel electrophoresis of the irradiated material in sodium dodecylsulfate (for example, 0.1%) may be used to evidence such cross-linking by a significant decrease in the amount of lower molecular weight material with the simultaneous appearance of high molecular weight material. While amino acid analysis of hydrolyzates of cross-linked proteinaceous material demonstrates a paucity of methionine, tyrosine and histidine (all destroyed by photo-catalytic oxidation), this reduction is not necessarily evidence of cross-linking. For example, if a protein is treated with $KI/I^2$ solution, derivatization of tyrosine and histidine occur, essentially eliminating these amino acids from an amino acid profile without cross-linking, as evidenced by the lack of change in the gel electrophoretic patterns.

Further evidence of cross-linking is provided by solubility and digestibility tests as known in the art. For instance, cross-linked collagen is generally insoluble such that solubility tests provide direct evidence of the degree of cross-linking. The digestibility tests involve incubation of the proteinaceous product with a proteolytic enzyme such as papain, trypsin, pepsin, or an enzyme known to specifically catalyze the degradation of hemoglobin or the particular oxygen binding/transport protein being cross-linked, and the subsequent testing of the media in which the product and enzyme are incubated for soluble degradation products of the cross-linked product. The test is generally accomplished by pelletizing the undigested, cross-linked product and the enzyme by centrifugation and testing the resulting supernatant for degradation products. The latter is particularly useful in light of the destruction of the amino acid histidine by photooxidation; analysis of the supernatant for histidine content and a comparison of that content to the amount of an amino acid such as hydroxyproline, which is not destroyed by photooxidation, in the supernatant provides a particularly sensitive assay for the degree of cross-linking. This comparison can be advantageously expressed as a ratio of histidine to hydroxyproline (his/hyp ratio), higher his/hyp ratios being indicative of more effective cross-linking.

The process disclosed herein is carried out in a batch, intermittent, or continuous manner. Following photo-irradiation, the cross-linked product is advantageously subjected to various treatments for the removal of the catalyst and other chemicals or impurities found therein before being used as a component in one of the blood supplements and/or substitutes listed above. Multiple rinses in a fresh buffer solution are, for example, used, followed by a least partial de-watering with, for instance, ethanol. The number of rinses and the volume of rinse solution required depends upon the mass of the tissue or the suspended material and the catalyst concentration utilized.

For purposes of completing this disclosure, all of the references cited hereinabove are hereby incorporated by reference. While the present invention has been described in detail for purposes of clarity and understanding, it will be clear to one skilled in the art from a reading of the disclosure that changes can be made in form and detail without departing from the true scope of the invention.

What is claimed is:

1. A composition of matter for use as either a substitute for or a supplement to blood made by a process for cross-linking an oxygen binding protein comprising:

incubating a sample of an oxygen binding protein to be cross-linked in an aqueous media solution of a photo-oxidative catalyst buffered to a pH of from about 6.8 to about 8.6 and irradiating the oxygen binding protein with light in the presence of oxygen for a period of time sufficient to cross-link the oxygen binding protein by transfer of electrons while maintaining the temperature of the media solution at between about −2° and about 40° C.

2. The composition of claim 1 wherein the pH is maintained in a range of from about 7.4 to about 8.0.

3. The composition of claim 1 wherein the oxygen concentration in the media is maintained during irradiation by maintaining the oxygen concentration of the atmosphere above the media at a concentration of from greater than 0 up to about 25%.

4. The composition of claim 1 wherein the oxygen concentration of the media during irradiation is maintained by maintaining the oxygen concentration of the atmosphere above the media at from about 5 to about 20%.

5. The composition of claim 1 wherein the oxygen binding protein is irradiated with a range of between about 100 and about 20,000 lumen hours.

6. The composition of claim 1 wherein the temperature is maintained between about 0° and about 25° C.

7. The composition of claim 1 wherein the oxygen binding protein is soaked in an aqueous buffer solution before being incubated in the aqueous media solution.

8. The composition of claim 7 wherein the osmolality of the buffer solution is from about 393 to about 800 mosm.

9. Artificial blood comprising an aqueous solution of salts, sugars and a cross-linked oxygen binding protein made by a process comprising:

soaking a sample of proteinaceous material including an oxygen binding protein in an aqueous medium having a high osmolality;

incubating the soaked proteinaceous material in an aqueous buffer including a photooxidative catalyst which, when excited by incident light cross-links the proteinaceous material; and irradiating the proteinaceous material in the aqueous buffer including the catalyst with light while holding the temperature and pH of the aqueous burlier at levels sufficient to maintain the oxygen concentration of the aqueous buffer so as to sensitize the catalyst into an excited state which is reduced by oxidative cross-linking of the proteinaceous material, the pH being maintained at between about 6.8 and about 8.6 and the temperature being maintained at between about −2° and about 40° C.

10. The artificial blood of claim 9 wherein the oxygen concentration of the atmosphere over the aqueous medium including the catalyst is maintained at a concentration between greater than 0 up to about 25% so as to maintain adequate oxygen concentration in the aqueous medium.

11. The artificial blood of claim 9 wherein the catalyst is dissolved in the aqueous buffer.

12. The artificial blood of claim 9 wherein the temperature is maintained at from about 0° to about 25° C.

13. The artificial blood of claim 9 wherein the osmolality of the aqueous medium is between about 393 and about 800 mosm.

14. The artificial blood of claim 13 wherein the pH of the aqueous medium is between about 7.4 and about 8.0.

* * * * *